US00PP14699P29

(12) United States Plant Patent
Dufresne

(10) Patent No.: US PP14,699 P2
(45) Date of Patent: Apr. 13, 2004

(54) SALVIA PLANT NAMED 'RFD-S018'

(50) Latin Name: *Salvia greggii*
Varietal Denomination: RFD-S018

(76) Inventor: Richard Frederick Dufresne, 313 Spuur Rd., Greensboro, NC (US) 27406

( * ) Notice: Subject to any disclaimer, the term of this patent is extended or adjusted under 35 U.S.C. 154(b) by 26 days.

(21) Appl. No.: 10/185,784

(22) Filed: Jun. 28, 2002

(51) Int. Cl.[7] ..... A01H 5/00
(52) U.S. Cl. ..... Plt./226
(58) Field of Search ..... Plt./226, 263

*Primary Examiner*—Bruce R. Campell
*Assistant Examiner*—June Hwu

(57) ABSTRACT

A new cultivar of Salvia plant named 'RFD-S018' that is distinguished by its rich, clear magenta rose color, dark purple-brown calyx and dense foliage. These traits set 'RFD-S018' apart from all other existing varieties of Salvia known to the inventor.

2 Drawing Sheets

Genus: Salvia.
Species: *greggii.*
Denomination: RFD-S018.

BACKGROUND OF THE INVENTION

The present invention relates to a new variety of *S. greggii* Gray, hereinafter referred to by the cultivar name 'RFD-S018'. 'RFD-S018' originated as a chance seedling from a potted plant found in the inventor's collection in a cultivated area of Greensboro, N.C., in March 1995. It was taken from the pot of a *S. greggii* Gray variety and maintained for asexual propagation purposes. The inventor presumes that 'RFD-S018' is a seedling of the adjacent plant, *S. greggii* Gray.

The inventor has been studying, collecting, and disseminating Salvia species for twenty-seven years. During this period, he has traded Salvia species and cultivars with many botanical gardens and nurseries.

One of the inventor's goals has been to sort out confusion on the identities of various forms of Salvias being marketed. This has necessitated developing contacts with various herbaria and taxonomic experts to assist with the proper identification of Salvia forms. The developed information has been supplied at times to Salvia collectors and to nurseries and botanic gardens where visits have been made to check on the correct identification of various Salvias.

Collected results of the identification of Salvias, along with horticultural information like zone hardiness, size, and bloom period and flower color have been reported in his publication, the Salvia Placard Handbook. Recently, the World of Salvia web site was created and is being maintained for the purpose of reporting this information about Salvias to the public.

The inventor has bred and introduced many successful commercial introductions, including *Salvia greggii* Gray hybrids 'Cherry Chief' (unpatented), 'Cherry Queen' (unpatented), 'Maraschino' (unpatented), and 'Raspberry Royale' (unpatented).

'RFD-S018' is distinguished from other varieties of the species known to the inventor and was selected for these distinguishing characteristics: namely, that the flowers of RFD-S018 are rich, clear magenta rose in color, in combination with a dark purple brown calyx that accents the flower and dense foliage.

'RFD-S018' was first asexually propagated in 1995 at Greensboro, N.C., USA using vegetative cuttings. It has been found to remain fixed, stable and uniform through several generations.

SUMMARY OF THE INVENTION

The following traits have been repeatedly observed and represent the distinguishing characteristics of 'RFD-S018'. In combination these traits set the new cultivar apart from all others existing varieties of Salvia known to the inventor. 'RFD-S018' has not been tested under all possible conditions and phenotypic differences may be observed with variations in environment, climatic, and cultural conditions, however, without any variance in genotype.

1. Salvia 'RFD-S018' exhibits a rich, clear magenta rose color.
2. Salvia 'RFD-S018' exhibits dark purple brown calyx.
3. Salvia 'RFD-S018' exhibits dense foliage.

BREIF DESCRIPTION OF THE DRAWINGS

The accompanying drawings illustrate the distinguishing traits of the new Salvia cultivar 'RFD-S018'. The photographs were taken in summer 2002 of a one year-old plant, in an 8" container that were grown a greenhouse in a cultivated area of Arroyo Grande, Calif., USA.

The drawing on sheet 1 illustrates the entire plant in summer with its dense foliage.

Sheet 2 is a close-up view of the flower. The drawings were made using conventional photographic techniques. Although colors may appear different from actual colors due to light reflectance, they are as accurate as possible by conventional photography.

BOTANICAL DESCRIPTION OF THE PLANT

The following is a detailed description of the Salvia plant named 'RFD-S018'. Data was collected in April 2001 from one year-old plants grown in one gallon containers in full sun at Greensboro, N.C., USA. Phenotypic differences may be observed with variation in environmental, climatic, and cultural conditions. The color determinations are in accordance with The 1986 Edition of The Royal Horticulture Society Colour Chart except where general color terms of ordinary dictionary significance are used. The growing requirements are similar to other Salvia plants.

Botanical classification: Salvia 'RFD-S018'.
Species: *greggii.*
Common Name: Salvia.
Use: Ornamental shrub.
Form: Bush.
Height: 0.8–1.2 meter.
Width: 0.7 meter.
Growth habit: Perennial.
Blooming season: From one month after breaking spring dormancy to first frost.
Lastingness of blooms: 3 to 4 days.
Disease and pest susceptibility: Drought tolerant. Deer and rabbit resistant. Susecptible to sucking insects when stressed. Generally, outgrows most bacterial and viral infections.
Stem:
*Color.*—187B.
*Shape.*—Rounded square.
*Diameter.*—0.8–1.3 mm.
*Texture.*—Smooth to minutely farinaceous.
Leaf:
*Arrangement.*—Opposite.
*Shape.*—Elliptic to oblong.
*Length.*—1.5–2.6 centimeters.
*Width.*—0.5–0.9 centimeters.
*Margin.*—Entire.
*Thickness.*—Slightly fleshy.
*Venation.*—Veins barely visible.
*Color* (*upper surface and lower surface*).—Varies between 137A and 137C.
*Apex.*—Shape: Acute or obtusely rounded. Color: RHS 137A to 137C.
*Base.*—Shape: Rounded to acuminate, sometimes oblique. Color: RHS 137A to 137C.
*Petiole.*—Shape: Mostly carinate; alate towards leaf base. Length: 7–10 millimeters. Width: 0.8–1.4 millimeters. Color: RHS 143C.
*Peduncle.*—Length: 4.7 mm. Width: 0.5 mm. Color: 145A. Texture: Glandular, puberulent.
Flower:
*Inflorescence.*—
*Type.*—Terminal raceme.
*Length.*—23 centimeters.
*Diameter.*—3.4–3.8 cm.
*Number.*—From 14 to 19 decussate pairs.
*Shape.*—Tubular, two-lipped.
Bud:
*Length* (*including calyx*).—13 mm.
*Length* (*immature flower.*).—1.5 mm.
*Width* (*immature flower*).—4 mm.
*Color* (*immature flower*).—66A.
*Shape* (*immature flower.*).—Hemisphere.
*Surface texture* (*immature flower*).—Prominently hairy.
Pedicel:
*Length.*—4.7 millimeters.
*Pedicel width.*—0.5 millimeters.
*Pubescence.*—Glandular, puberulent.
*Color.*—RHS 145A.
Calyx:
*Shape.*—Tapered cylinder, flared toward the apex.
*Rib number.*—10, longitudinal.
*Length.*—From 9 mm to 13 mm.
*Width.*—From 4.5 mm to 5.5 mm.
*Pubescence.*—Glandular, puberulent.
*Color.*—Base and between ribs: 145B. Tip and ribs: 183A.
*Lobe.*—Upper: Number: 1. Shape: Acute. Length: 3.8 millimeters. Width: 2.4 millimeters.
*Lower.*—Number: 2. Shape: Acute. Length: 3.4 millimeters. Width: 3.1 millimeters.
Corolla:
*Shape.*—Tubular proximally to two-lipped distally.
*Length.*—3.18 centimeters.
*Diameter* (*maximum width of lower lip.*).—17.3 mm.
*Color range.*—Magenta RHS 66A.
*Tube.*—Length: 19.5 millimeters. Width (measured directly under magnifying lens): 3.0 millimeters. Depth: 6.5 millimeters. Lip: Upper Number: 1. Shape: Hood-like. Length: 11.8 millimeters. Lower Number: 2 suborbicular. Shape: Banner-like, extended downward. Outline: Obovate. Length: 17.1 millimeters. Diameter at widest point: 17.3 millimeters. Depth: 7.6 millimeters.
Reproductive organs:
*Pistil.*—Stigma color: 65D.
*Style.*—Length: 3.2 centimeters. Color: 66C. Pubescence: Present toward tip. Attachment site: To a four-lobed ovary between the lobes. Ovary color: 145B.
*Stamen.*—Number: 2. Shape: Seesaw-like. Connective length: 12.3 millimeters. Filament length: 4.1 millimeters. Anther: Color: 158D. Attachment site: Outer end of the connective. Pollen: Color: 13A. Staminodes: Present (weak). Invagination: Present (weak, barely noticeable). Fertility: 2–4 glossy brown-black oblong-elliptic nutlets.
*Nutlets.*—Length: 4 mm. Width: 2 mm. Color: 200A. Shape: Oblong-elliptic.

I claim:

1. A new and distinct cultivar of Salvia plant named 'RFD-S018' as described and illustrated.

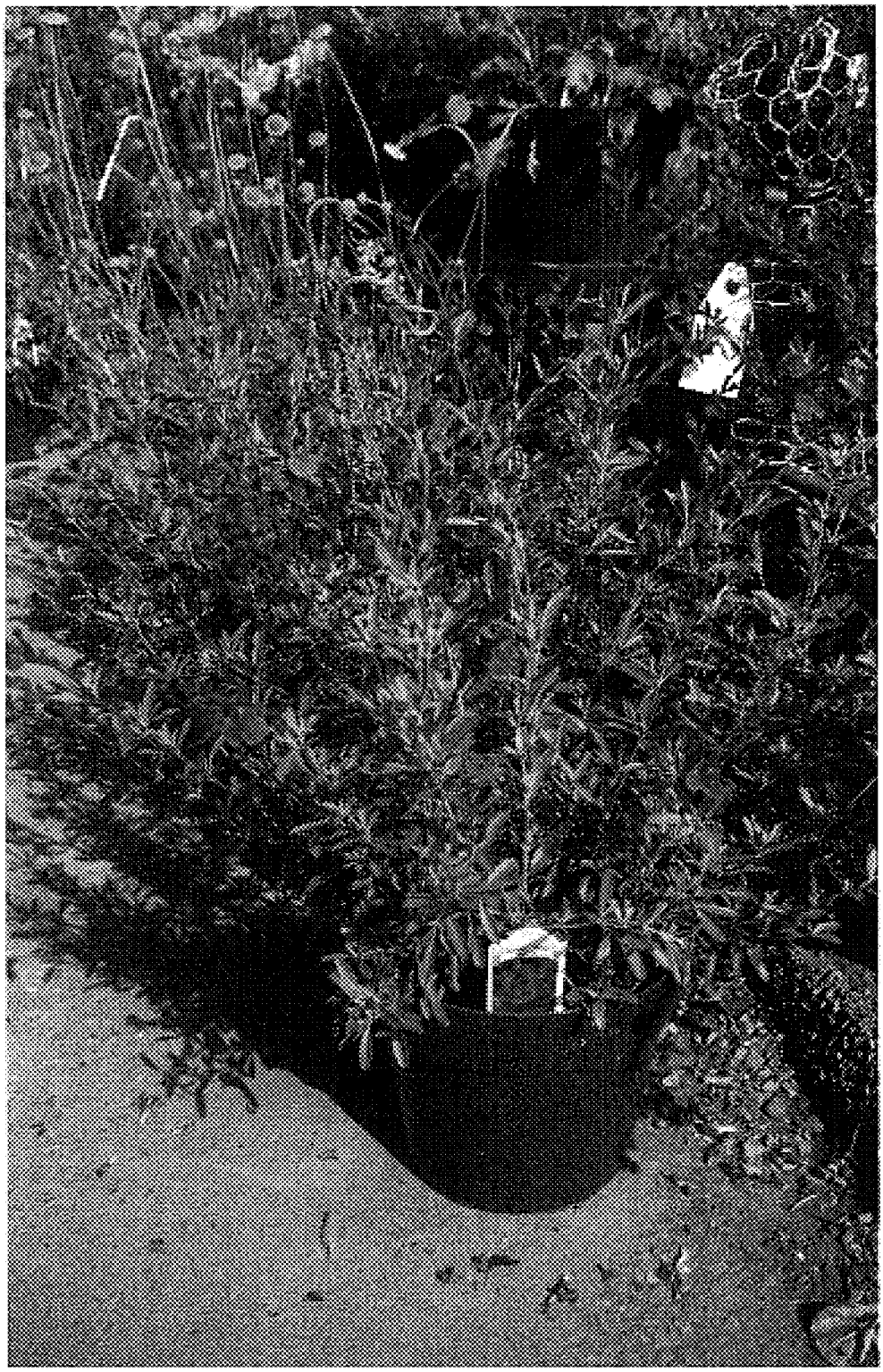

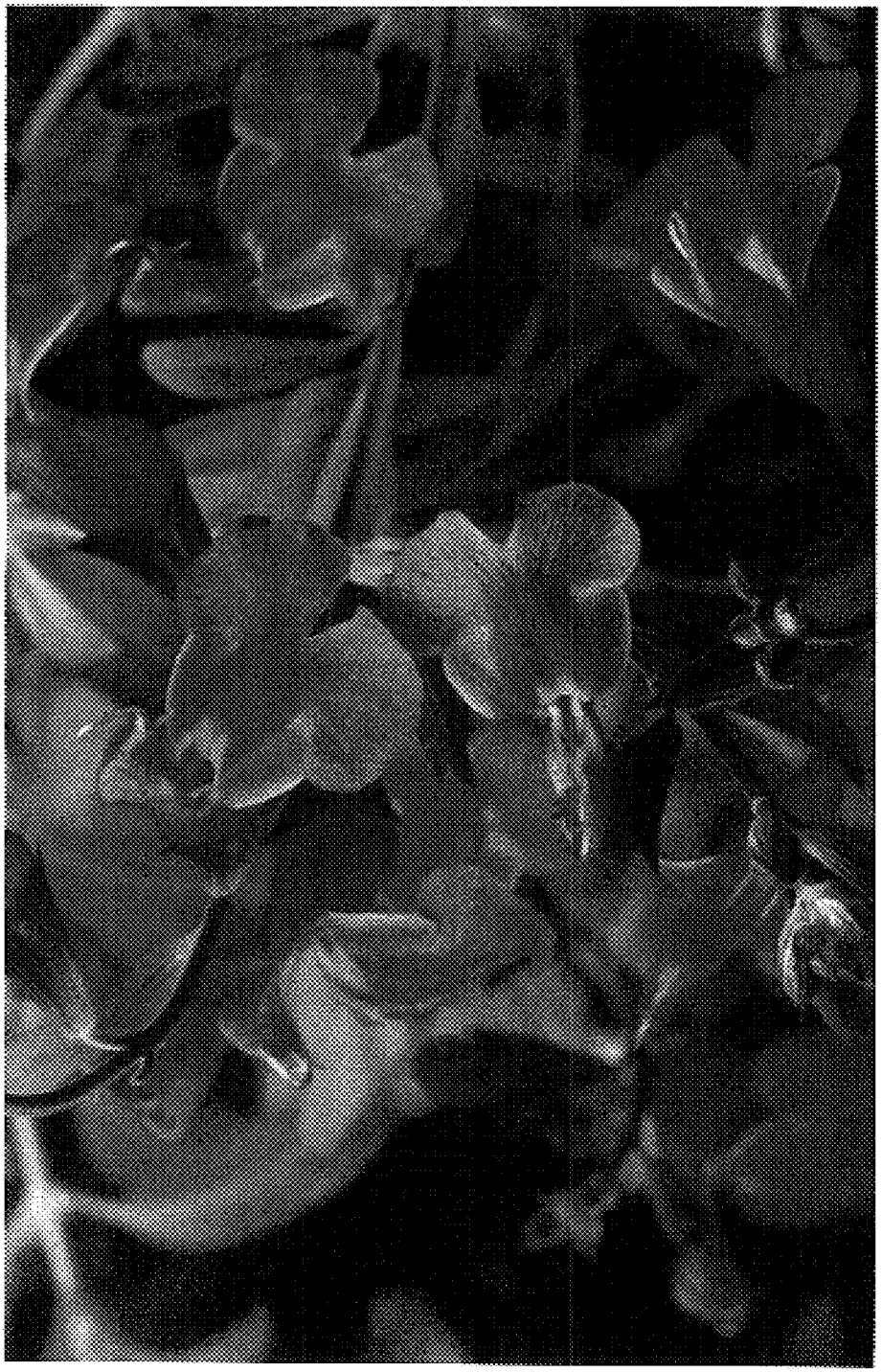

* * * * *